United States Patent
Zhang et al.

(10) Patent No.: US 10,725,005 B2
(45) Date of Patent: Jul. 28, 2020

(54) SINGLE BODY QUADRUPLE CYLINDER TRITIUM MEASURING APPARATUS

(71) Applicant: Xiaowei Zhang, Oakville (CA)

(72) Inventors: Xiaowei Zhang, Oakville (CA); Jiangrong Wu, Oakville (CA); Sabatino Nacson, Thornhill (CA)

(73) Assignee: Xiaowei Zhang, Ontario (CA)

( * ) Notice: Subject to any disclaimer, the term of this patent is extended or adjusted under 35 U.S.C. 154(b) by 182 days.

(21) Appl. No.: 15/981,717

(22) Filed: May 16, 2018

(65) Prior Publication Data

US 2018/0335414 A1   Nov. 22, 2018

Related U.S. Application Data

(60) Provisional application No. 62/507,023, filed on May 16, 2017.

(51) Int. Cl.
| | | |
|---|---|---|
| *G01N 33/00* | (2006.01) | |
| *G01T 1/178* | (2006.01) | |
| *G01T 1/185* | (2006.01) | |

(52) U.S. Cl.
CPC ..... *G01N 33/0055* (2013.01); *G01N 33/0062* (2013.01); *G01T 1/178* (2013.01); *G01T 1/185* (2013.01); *G01N 2033/0068* (2013.01)

(58) Field of Classification Search
CPC ........... G01N 33/0055; G01N 33/0062; G01N 2033/0068; G01T 1/178; G01T 1/185
See application file for complete search history.

(56) References Cited

U.S. PATENT DOCUMENTS

| | | | | |
|---|---|---|---|---|
| 2,599,922 A | * | 6/1952 | Kanne ..................... | H01J 47/02 250/380 |
| 4,091,283 A | * | 5/1978 | Sun .......................... | G21H 5/02 250/303 |

(Continued)

FOREIGN PATENT DOCUMENTS

DE   2723998 A1 * 11/1978 ............. H01J 47/02

OTHER PUBLICATIONS

Model 400SBDyC datasheet [online]. Overhoff Technology Corp, available online Apr. 18, 2012 [retrieved on Mar. 26, 2020]. Retrieved from the Internet: <URL: http://www.overhoff.com/uploads/Model.400SBDyC.uCi.pdfl>. (Year: 2012).*

(Continued)

*Primary Examiner* — Christine S. Kim
(74) *Attorney, Agent, or Firm* — Christensen, Fonder, Dardi & Herbert PLLC; Douglas Christensen

(57) ABSTRACT

A tritium-in-air measuring apparatus for measuring a concentration of tritium in air, the measuring apparatus comprising a sensing apparatus for sensing the concentration of tritium in the air and producing at least one signal representing the concentration; a signal processing apparatus, operatively connected to the sensing apparatus, for receiving the signal, processing the signal, and outputting an indication of the concentration of tritium; the sensing apparatus comprising four equal-dimensioned ion chambers, the four chambers being formed in a single block of metal, the four chambers comprising a first measurement chamber, a second measurement chamber, a first compensation chamber and a second compensation chamber.

14 Claims, 3 Drawing Sheets

(56) References Cited

U.S. PATENT DOCUMENTS

| | | | | |
|---|---|---|---|---|
| 5,093,570 | A | * | 3/1992 | Dorfi .................... G01T 1/14 250/253 |
| 6,734,433 | B1 | * | 5/2004 | Meunier ............... H01J 47/026 250/374 |
| 2011/0062345 | A1 | * | 3/2011 | Paglieri .................... G01T 1/00 250/395 |
| 2013/0008314 | A1 | * | 1/2013 | Guillemant ............ G21D 1/003 96/19 |

OTHER PUBLICATIONS

Model 606 Datasheet [online[. Sensetecz Engineering, available online 2018 [retrieved on Mar. 26, 2002]. Retrieved from the internet: <URL: http://sensetecz-engineering.com/product/portable-tritium-monitor/> (Year: 2018).*

Anthony, J.D, Portable Tritium Monitor has Gamma Compensation, Apr. 1959, Instrumentation and Measurement, pp. 120-122. (Year: 1959).*

* cited by examiner

SINGLE BODY QUADRUPLE CYLINDER TRITIUM MEASURING APPARATUS

CROSS REFERENCE TO RELATED APPLICATIONS

This application claims priority to U.S. Provisional Application No. 62/507,023 filed May 16, 2017 to ZHANG et al., entitled "Single Body Quadruple Cylindrical Ion Chamber Tritium Gas Monitor," incorporated herein by reference.

FIELD OF THE INVENTION

The present invention relates to the field of tritium detection, and in particular, to tritium-in-air detection.

BACKGROUND OF THE INVENTION

Tritium is a radioactive isotope of hydrogen. Because it is relatively weakly radioactive, it is generally not considered dangerous externally. However, if concentrations are too high, it can be dangerous if inhaled or ingested. In some cases, the main concern is tritium water vapour in the air. In other cases, both tritium gas and tritium water may be of concern. Thus, tritium-in-air detectors have been designed to monitor the levels of tritium in the air that may be inhaled.

Prior art detectors deal with the problems created by background Gamma radiation, and beta radiation (which comes from noble gases in the air). Because the signal from tritium—even from dangerous levels of tritium—can be very low relative to gamma and beta radiation, existing devices include features to compensate for these other types of radiation. For example, in a 1-liter ion chamber, the sensitivity of tritium is 1 fA (femto Apmere, which is $1 \times 10^{-15}$ Amperes). The Gamma background signal, which is non-uniform, could be 1100 fA, while the beta radiation background signal could be 3000 fA. Thus, prior art devices were designed with quadruple ion chambers to provide high gamma compensation. Noble gas compensation is achieved by injecting dry air into the compensation chambers. Examples of existing prior art detectors which have some or all of these features are the Overhoff Technology Corporation Model 400S BDγC detector, and the Tyne Engineering Model 7043 detector.

The Overhoff detector uses quadruple ion chambers that are separate and made up of square metal cups. The shell of the measuring pair of ion chambers is connected to a negative battery terminal and the shell of the compensation pair of ion chambers is connected to a positive battery terminal. All four central rods from each of the four ion chambers are connected together. Ideally, the positive charge from the measuring chambers is equal to the negative charge from the compensation chambers caused by Gamma and beta background radiation.

The Tyne detector consists of quadruple ion chambers made of separate cylindrical tubes fastened together for low tritium range and a small central tube for high tritium range. All shells of the tubes are connected together electrically to the negative terminal of a battery. Each central rod of each chamber is connected to a pre-amplifier to convert electrical charge to voltage. The four voltage signals coming from the pre-amplifier are fed to a computer to do Gamma compensation, beta radiation compensation and tritium signal processing.

SUMMARY OF THE INVENTION

According to one aspect of the invention, there is provided a tritium-in-air measuring apparatus for measuring a concentration of tritium in air, the measuring apparatus comprising: a sensing apparatus for sensing the concentration of tritium in the air and producing at least one signal representing the concentration; a signal processing apparatus, operatively connected to the sensing apparatus, for receiving the signal, processing the signal, and outputting an indication of the concentration of tritium; the sensing apparatus comprising four equal-dimensioned ion chambers, each ion chamber preferably comprising a cylinder, the four chambers being formed in a single block of metal, the four chambers comprising a first measurement chamber, a second measurement chamber, a first compensation chamber and a second compensation chamber.

Optionally, the metal comprises stainless steel. Optionally, the sensing apparatus further comprises a central anode rod positioned in each cylinder, a grounding plate at the base of each cylinder, and a cathode, associated with each cylinder, comprising the wall of the cylinder, wherein, for each cylinder, the rod, the grounding plate and the cathode are mutually electrically isolated. Optionally, the at least one signal comprises the current in each rod. Optionally, the concentration is represented by the sum of the currents in the rods of the measurement cylinders less the sum of the currents in the rods of the compensation cylinders. Optionally, the sensing apparatus comprises an airflow pathway from an outside of the apparatus into the first measurement cylinder, and out of the first measurement cylinder into the second measurement cylinder, and out of the second measurement cylinder to the outside, the sensing apparatus further comprising an airflow generator for moving air along the airflow path. Optionally, the sensing apparatus further includes an air dryer to remove moisture from air passing through the compensation cylinders, and wherein the sensing apparatus comprises an airflow pathway from an outside of the apparatus into the first measurement cylinder, and out of the first measurement cylinder into the second measurement cylinder, and out of the second measurement cylinder into the air dryer, and out of the air dryer into the first compensation cylinder, and out of the first compensation cylinder into the second compensation cylinder, and out of the second compensation cylinder to the outside, the sensing apparatus further comprising an airflow generator for moving air along the airflow path. Optionally, the sensing apparatus further includes a relative humidity sensor on the airflow pathway between the air dryer and the inlet to the first compensation cylinder, the relative humidity sensor being configured to display a relative humidity between zero and one hundred percent of the air entering the first compensation cylinder from the air dryer, whereby the functioning of the air dryer can be easily monitored.

According to another aspect of the invention, there is provided a tritium-in-air measuring apparatus for measuring a concentration of tritium in air, the measuring apparatus comprising: a sensing apparatus for sensing the concentration of tritium in the air and producing at least one signal representing the concentration; a signal processing apparatus, operatively connected to the sensing apparatus, for receiving the signal, processing the signal, and outputting an indication of the concentration of tritium; the sensing apparatus comprising four equal-dimensioned ion chambers, each ion chamber comprising a cylinder, the four chambers comprising a first measurement chamber, a second measurement chamber, a first compensation chamber and a second compensation chamber; wherein the sensing apparatus further includes an air dryer to remove moisture from air passing through the compensation chambers, and wherein the sensing apparatus comprises an airflow pathway from an outside of the apparatus into the first measurement chamber, and out of the first measurement chamber into the second measurement chamber, and out of the second measurement chamber into the air dryer, and out of the air dryer into the first compensation chamber, and out of the first compensation chamber into the second compensation chamber, and out of the second compensation chamber to the outside, the sensing apparatus further comprising an airflow generator, for example, a pump, for moving air along the airflow path; the sensing apparatus further comprising a pressure compensation apparatus for determining a measurement normalization coefficient for normalizing a measured signal, and a compensation normalization coefficient for normalizing a compensation signal. Optionally, the pressure compensation apparatus comprises a first absolute pressure sensor for measuring the absolute pressure at an inlet to the first measurement chamber, a second absolute pressure sensor for measuring an absolute pressure at an inlet to the first compensation chamber, and a differential pressure sensor for measure pressure difference between an outlet of the second measurement chamber and the inlet of the first measurement chamber. Optionally, the measurement normalization coefficient is determined according to the formula $P_{ATM}(AP_1+DP/2)$ wherein $P_{ATM}$ is mean atmospheric pressure at sea level, AP1 is the pressure measured by the first absolute pressure sensor, and DP is the pressure difference measured by the differential pressure sensor. Optionally, the compensation normalization coefficient is determined according to the formula $P_{ATM}/(AP_2+DP/2)$ wherein $P_{ATM}$ is mean atmospheric pressure at sea level, $AP_2$ is the pressure measured by the second absolute pressure sensor, and DP is the pressure difference measured by the differential pressure sensor.

According to another aspect of the invention, there is provided a tritium-in-air measuring apparatus for measuring a concentration of tritium in air, the measuring apparatus comprising: a sensing apparatus for sensing the concentration of tritium in the air and producing at least one signal representing the concentration; a signal processing apparatus, operatively connected to the sensing apparatus, for receiving the signal, processing the signal, and outputting an indication of the concentration of tritium; the signal processing apparatus including an analog-to-digital converter for converting the signal from an analog form to a digital form, the converter having a resolution of at least 18 bits. Optionally, the signal processing apparatus comprises a 32-bit microcontroller. Optionally, the signal processing apparatus comprises a preamplifier for amplifying the signal entering the analog-to-digital converter.

According to another aspect of the invention, there is provided a method of manufacturing a quadruple cylindrical ion chamber unit for use in a tritium-in-air measurement apparatus, the method comprising the steps of (1) providing a single block of metal; and (2) machining the block to form four equal-dimensioned cylindrical ion chambers in cruciform arrangement.

DETAILED DESCRIPTION OF THE PREFERRED EMBODIMENTS

Described herein in detail is a tritium-in-air measuring apparatus for measuring a concentration of tritium in air. The measuring apparatus 10 generally comprises a sensing apparatus for sensing the concentration of tritium in the air and producing at least one signal representing the concentration; and a signal processing apparatus, operatively connected to the signal detection apparatus, for receiving the at least one signal, processing the signal, and outputting an indication of the concentration of tritium.

Figure 1:
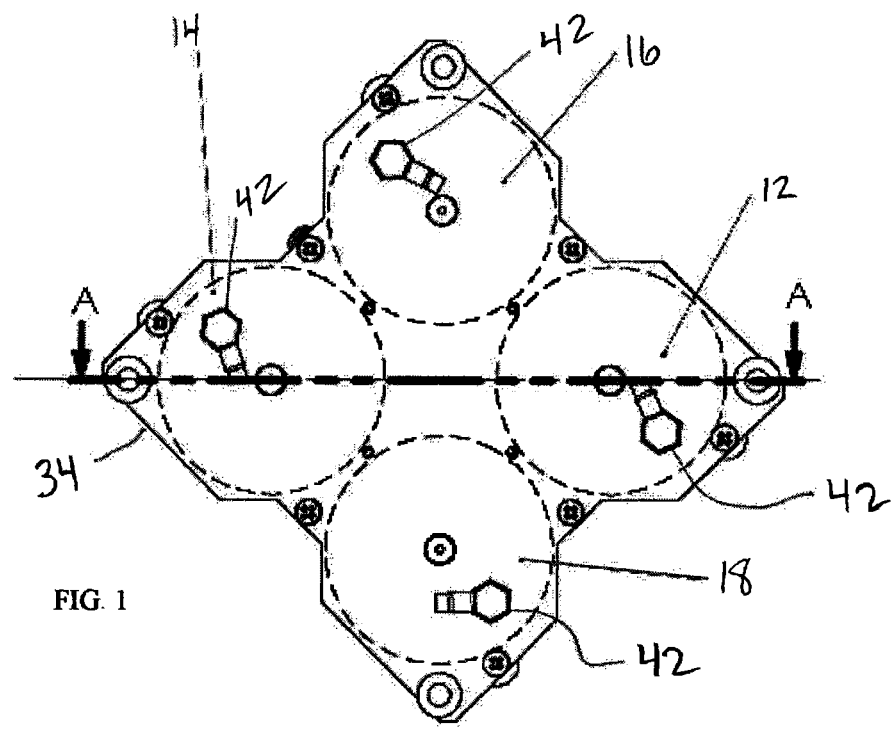
FIG. 1 is a top view of the tritium in air detector of the present invention.
Figure 2:
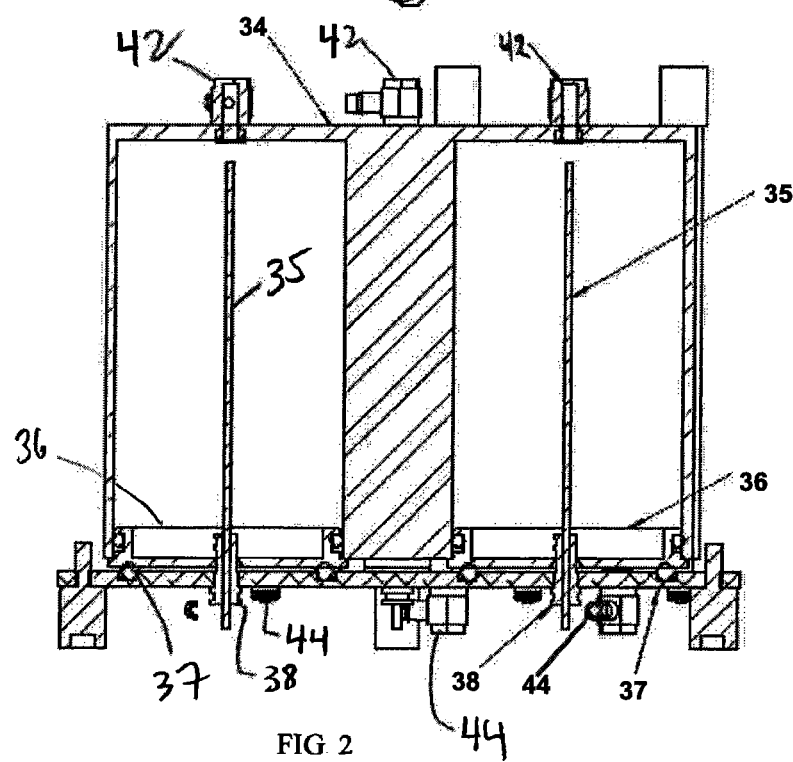
FIG. 2 is a cross-sectional view of the tritium-in-air detector taken along line A-A of FIG. 1.
Figure 3:
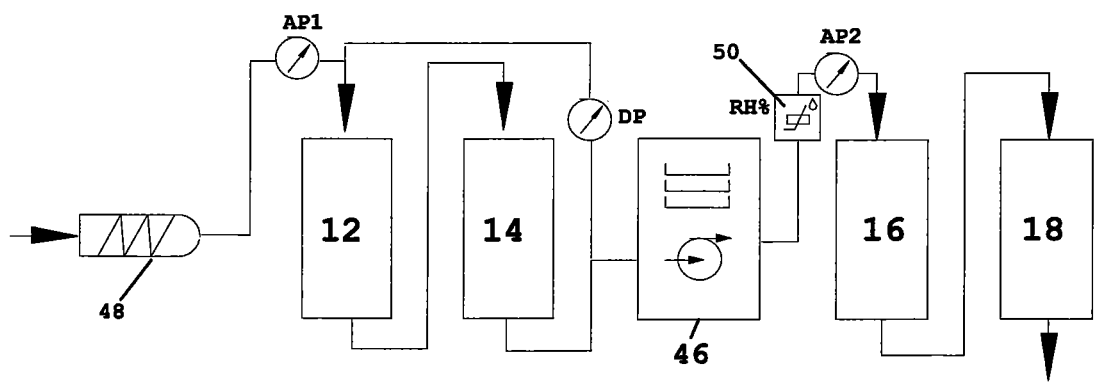
FIG. 3 is a schematic diagram of aspects of the sensing apparatus forming part of the invention.

Referring now to FIGS. 1, 2 and 3, aspects of the preferred sensing apparatus are shown. The measuring apparatus 10 includes a first measuring chamber 12, a second measuring chamber 14, a first compensation chamber 16 and a second compensation chamber 18. The chambers are most preferably equally-dimensioned (i.e. equal to one another in all of their dimensions). The chambers are each preferably cylindrical, preferably 1.9 inches in diameter and 3.475 inches deep. It will be appreciated that other sizes are comprehended by the invention. Preferably, their walls are polished to a mirror finish to minimize tritium deposition in the walls of the chambers.

Each ion chamber preferably includes a centrally positioned anode rod 35 in which current is generated by the radiation. The rod 35 is preferably mounted at the bottom of the ion chamber, and electrically isolated from the chamber wall and grounding plate 37 by means of Teflon feed through 38. For each chamber, a precision pre-amplifier on a printed circuit board is mounted on grounding plate 37, and directly accepts the current input from the four rods 35. In this embodiment, the current in each rod 35 is the at least one signal represents the concentration of tritium as described below, and the preamplifier forms part of the signal detection apparatus.

In the preferred embodiments the wall of each ion chamber is connected to a battery or to some other voltage source so as to be negatively charged, so that the wall acts as the cathode in the ion chamber. The typical voltage in the ion chamber walls for use in the preferred measurement apparatus is negative 48V.

Each ion chamber is enclosed by four metal caps 36 and the respective grounding plate 37. Each ion chamber is preferably closed at its top (because the cylinders are preferably machined from the bottom—see below). At the tops of each cylinder are mounted gas outlet fittings 42 for passing air out of each chamber. At the bottom of each ion chamber is a gas inlet 44 for passing air into each ion chamber. The inlets and outlets are connected to create an airflow path a shown, in preferred form, in FIG. 3. Preferably, the outlets 42 and inlets 44 are connected by silicone tubing, so that the airflow path is as follows. Air travels into the bottom of and then out of the top of measuring chamber 12, into the bottom of then out the top of measuring chamber 14, through an air dryer 46, into the bottom of and out the top of compensation chamber 16, and into the bottom of and out the top of compensation chamber 18.

This airflow pathway is preferred if the main concern for the measuring apparatus 10 is to measure concentration of tritium water in the air, which would typically be in the form of vapour and/or droplets. In this configuration, tritium water is removed by the air dryer 46, so that when the air enters the compensation chambers, it is substantially free of tritium water ($H^3HO$ or other combinations). However, tritium gas ($T_2$) will enter the compensation chambers, so that its concentration will not be measured by the apparatus 10, but rather, it will be compensated out of the measurement. If it is desired to measure the concentration of tritium water and tritium gas ($T_2$) together, then the airflow pathway can terminate after the outlet 44 from measuring chamber 14, the second measuring chamber. The compensation chambers can operate to compensate for gamma radiation without air passing through them.

It will be appreciated that the apparatus preferably includes an air pump to move the air along the airflow pathway. In the preferred embodiment shown in FIG. 3, the pump is associated with air dryer 46. The pump pulls air through measuring chambers 12, 14, through the dryer 46, and then pushes the air through compensation chambers 16, 18. In the alternate embodiment where the airflow pathway does not include the compensation chambers, the pump pulls air through the two measuring chambers. It will be appreciated, however, that other configurations are comprehended by the invention including, for example, a pump separate from the dryer 46, and a pump positioned at a different location while still operating to move air along the airflow pathway.

In the preferred embodiment, the air moving through the sensing apparatus is ambient air, because ambient tritium concentration is what is typically being monitored. The sensing apparatus includes a dust and particle filter 48 through which the air is pulled prior to entering the first measuring chamber 12.

As shown in FIG. 1, the preferred form of the sensing apparatus is to have two measuring chambers opposite one another, and two compensation chambers opposite one another, with the four chambers being in cruciform arrangement. The reason for having two of each type of chamber, in this arrangement, is that this arrangement improves background compensation. It is possible in particular circumstances for certain radiation sources to be localized or directional. For example, if there is gamma radiation coming from a particular direction, the presence of two of each kind of chamber opposite one another in cruciform arrangement help even out the signal produced in each chamber. With only one of each kind of chamber, there would be a higher risk of the aforementioned gamma radiation registering as higher in the measurement chamber than in the compensation chamber, or vice versa, thus introducing error. For this same reason, preferably, the ion chambers are position as near to one another as is practically possible.

It will be appreciated that one source of error in measuring tritium levels is having slightly different actual volumes in the measurement chambers versus the compensation chambers. Such volume differences may be the result of imprecision in the manufacturing of the detector and the ion chambers. For example, if a measurement apparatus has a 2% difference between the volumes of the measurement and compensation chambers, 2% of the beta and gamma signal will be erroneously attributed to tritium. In conditions of 10 mR/hour background gamma radiation, and 3000 fA of noble gas signal, the total error would be 88 $\mu Ci/m^3$. Thus, Tritium levels below that level of error would be unmeasurable by such a measurement apparatus.

Preferably, the four ion chambers are formed in a single block of metal. The present inventors have discovered that differences in volume between cylinders are less likely to occur, and if they do, they are less likely to be substantial, if the cylinders are formed in a single block (i.e. piece or chunk) of metal. The metal is preferably stainless steel. The formation of the cylinders is preferably accomplished by means of providing the block of metal, and then machining it to produce the four equally dimensioned cylinders in cruciform arrangement as described above. This results in a single body construction of the four cylinders.

This unitary arrangement (i.e. the four cylinders are formed in a single block 34, with the cylinders and "housing" being a single piece), has been found to provide superior reliability in producing equal-dimensioned ion chambers. By contrast, making each cylinder out of different pieces, and/or combining four independent cylinders together to make the cruciform arrangement, has been found to result more often in substantial dimensional differences in the cylinders that produce measurement error.

Figure 4:
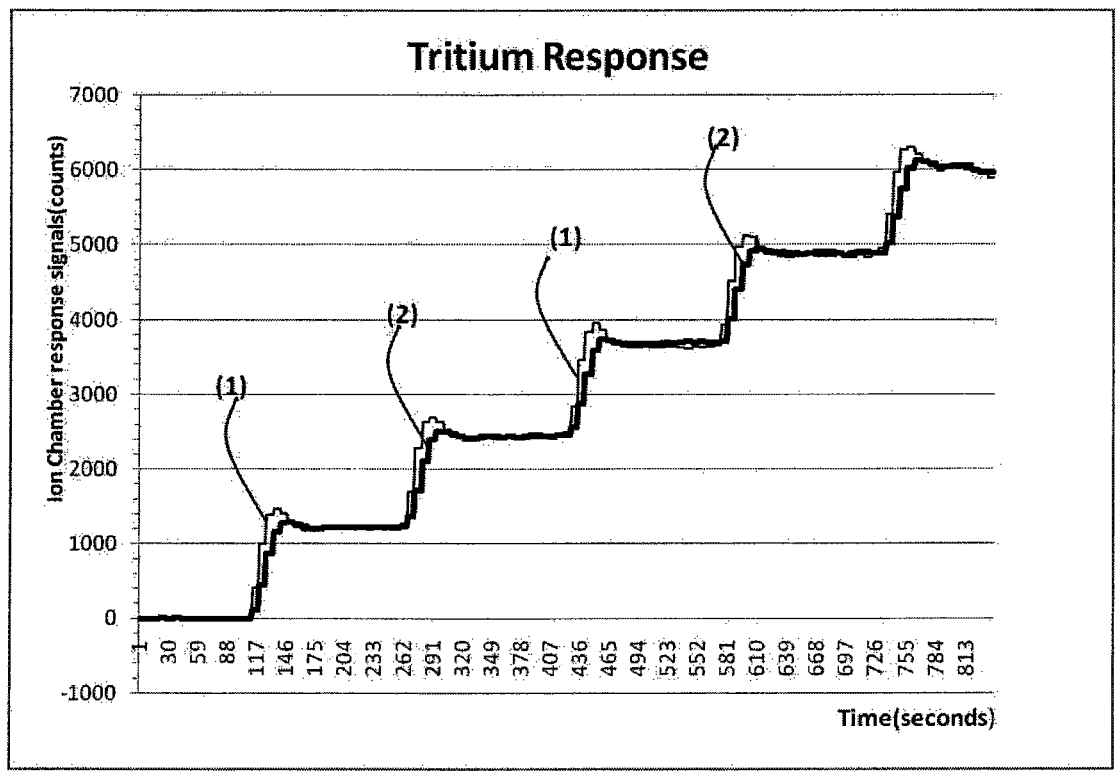
FIG. 4 is a graph showing a test output of a prototype of the preferred form of the invention.

A prototype measuring apparatus as generally described herein, including the single block unitary arrangement was built and tested. For tritium calibration, five concentration levels of tritium gas (1080, 2130, 3150, 4200, 5230 $\mu Ci/m3$) were injected into the first measuring chamber and second measuring chamber. The compensation chambers were sealed to allow for compensation of background Gamma radiation. Response signal (1) shows the response of the first measuring chamber, and the response signal (2) shows the response of the second measuring chamber. The units are in analog to digital counts. FIG. 4 shows the responses of the two measuring chambers as a function of time. As FIG. 4 shows, the responses of the first and second measuring chambers are highly uniform and stable, which is desirable, suggesting that the unitary construction provides uniform performance and improved compensation.

The Gamma response of each ion chamber was also evaluated, and the results are shown in Table 1. The gamma radiation from a cesium 137 source was aimed to the central line of quadruple ion chamber. The value of current from each ion chamber was sent to a computer through the RS232 port built into the prototype unit. The cesium 137 source was exposed at different distances to assess the effect of compensation method of the unit. The four ion chamber responses to Gamma radiation were in close agreement measured in femto-ampere current (1 femto-ampere is 10-15 A). This again suggests the advantages of having uniform construction of the chambers in proximity and identical volumes.

TABLE 1

| Gamma Injection (mR/Hour) | Measuring Chamber 1 response (fA) | Measuring Chamber 2 response (fA) | Compensation Chamber 1 response (fA) | Compensation Chamber 2 response (fA) | Gamma Compensated Tritium Reading ($\mu Ci/m^3$) |
|---|---|---|---|---|---|
| 0.2 | 0.890 | 0.919 | 0.914 | 0.953 | −0.178 |
| 0.6 | 2.196 | 2.222 | 2.185 | 2.137 | 0.293 |
| 1.4 | 3.098 | 3.093 | 3.090 | 3.061 | 0.127 |
| 1.8 | 3.235 | 3.237 | 3.148 | 3.116 | 0.640 |
| 6.2 | 8.966 | 9.193 | 9.159 | 9.319 | −0.986 |

Another aspect of the preferred embodiment is pressure compensation (see FIG. 3). Ambient air with traces of tritium gas enters the system through the front dust filter and absolute pressure sensor AP1 measures the pressure before entrance into first and second measuring chambers. The front filter and the chambers' gas inlets and outlets restrict the air flow causing a small pressure change inside the first and second measuring chambers. This causes a reduced pressure inside these chambers lower than atmospheric pressure. A similar restriction affects first and second compensation chambers 1 and 2, which would be at a higher pressure than atmosphere. A typical flow rate of 1.5 liter/minute would result in a pressure difference between measuring and compensation chambers of approximately 2 kPa. This difference in pressure would impact tritium error reading of 2%. The reason is that if pressure differs between chambers, there will be different masses of air in those chambers, with the tritium concentration readings being biased accordingly. The present invention thus includes a pressure compensation apparatus and method for normalizing the measured and compensation signals in the four chambers according to the measured pressure difference, to correct the error introduced by these pressure changes.

As shown in FIG. 3, sensor AP1 is configured and positioned to measure the absolute pressure at the inlet to the first measuring chamber. Sensor DP is configured and positioned to measure the pressure difference between that inlet and the outlet from the second measuring chamber. Sensor AP2 is configured and positioned to measure the absolute pressure at the inlet to the first compensation chamber.

The readings are used to calculate two normalization coefficients, by which the measured and compensation signals are multiplied to normalize them to correct for the pressure changes. The measurement normalization coefficient is determined according to the formula $P_{ATM}$ ($AP_1$+ DP/2), wherein $P_{ATM}$ is mean atmospheric pressure at sea level (101.3 kPa), AP1 is the pressure measured by the first absolute pressure sensor AP1, and DP is the pressure difference measured by the differential pressure sensor DP. The compensation normalization coefficient is determined according to the formula $P_{ATM}$ ($AP_2$+DP/2), wherein $AP_2$ is the pressure measured by the second absolute pressure sensor AP2.

The pressure compensation apparatus may take different forms than the preferred form described above, and the sensors used may take different physical forms than the preferred pressure compensation apparatus described above.

The preferred sensing apparatus includes a relative humidity sensor 50 configured and positioned to measure the relative humidity of the air entering the first compensation chamber from the air dryer, and display a numerical relative humidity of the air (i.e. between 0 and 100). Air dryers have a tendency toward reduced effectiveness over time. Meanwhile, if tritium water concentrations are the main concern, then the air dryer not working properly can have negative consequences on the accuracy of the measurements, because it is desirable in such circumstances to remove substantially all of the tritium water from the air before it enters the compensation chambers. Thus, the humidity sensor 50 makes it easier for the user to ascertain the level of effectiveness of the air dryer, and to take action if any is needed.

Figure 5:
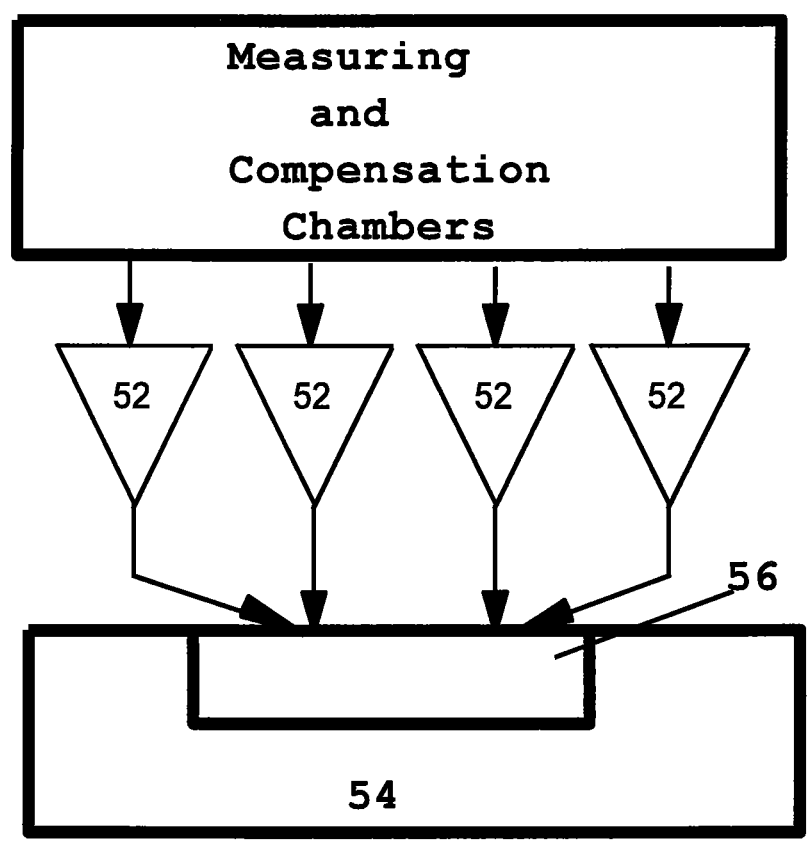
FIG. 5 is a schematic diagram of aspects of the preferred signal processing apparatus forming part of the invention.

Referring now to FIG. 5, in the preferred embodiment, the signal processing apparatus includes four preamplifiers 52, one for each ion chamber, which current directly from rods 35. The preamplifiers 52 amplify the current (typically very small and measured in femto Amperes). The output of the preamplifiers 52 is preferably fed to a microcontroller 54. One suitable microcontroller is the 32-bit model MKL25 made by Freescale Semiconductor Inc. The preferred microcontroller includes a built in analog-to-digital converter (ADC) 56, though other arrangements are comprehended.

The preferred ADC is a 16-bit ADC. Preferably, the signals incoming from the preamplifiers 52 are oversampled. For example, the sampling rate may be 2160 samples per second, or more. The preferred ADC resolution thus reaches at least 18 bits, and preferably has a high SNR—most preferably at least 120 dB.

In the preferred signal processing apparatus, the ADC converts the analog signals to digital. The tritium concentration being measured is preferably calculated by adding the two measuring chamber signals together and multiplying them by the corresponding normalization coefficient mentioned above; adding the two compensation chamber signals together and multiplying them by the corresponding normalization coefficient mentioned above; and subtracting the normalized compensation sum from the normalized measuring sum to obtain the result representing the tritium concentration. Alternatively, the calculation could use averages of the measuring and compensation signals, rather than sums.

It will be appreciated that the high resolution ADC with high SNR permits detection of a wide range of tritium concentrations without range switching as is seen in the prior art. In the prior art, the signal processing equipment cannot handle a wide range of results, and separate amplifiers, and even separate ion chambers, are required to read high concentrations. In the present preferred embodiment, no range switching is required to read tritium concentrations of 0 to 200,000 $\mu Ci/m^3$, which is a range required in a number of applications. With 18 bit resolution, the ADC is capable of producing over 260,000 distinct values, and thus, the need for range switching can be avoided for the aforementioned range.

It will be appreciated that the invention is not limited to the preferred embodiments described herein. Rather the invention comprehends the entire breadth of the disclosure. The various features of the described apparatus can be combined in all possible combinations and still be comprehended by the invention.

The invention claimed is:

1. A tritium-in-air measuring apparatus for measuring a concentration of tritium in air, the measuring apparatus comprising:
   a sensing apparatus for sensing the concentration of tritium in the air and producing at least one signal representing the concentration; and
   a signal processing apparatus, operatively connected to the sensing apparatus, for receiving the signal, processing the signal, and outputting an indication of the concentration of tritium,
   the sensing apparatus comprising four equal-dimensioned ion chambers, the four ion chambers being formed in a single block of metal, and the four ion chambers comprising a first measurement chamber, a second measurement chamber, a first compensation chamber and a second compensation chamber.

2. A measuring apparatus as claimed in claim 1, wherein the metal comprises stainless steel.

3. A measuring apparatus as claimed in claim 1, wherein each of the ion chambers comprises a cylinder.

4. A measuring apparatus as claimed in claim 3, wherein the sensing apparatus further comprises a central anode rod positioned in each cylinder, a grounding plate at the base of each cylinder, and a cathode, associated with each cylinder, comprising the wall of the cylinder, wherein, for each cylinder, the rod, the grounding plate and the cathode are mutually electrically isolated.

5. A measuring apparatus as claimed in claim 4, wherein the at least one signal comprises a current in each rod.

6. A measurement apparatus as claimed in claim 5, wherein the concentration is represented by a sum of currents in the rods of the measurement cylinders less a sum of currents in the rods of the compensation cylinders.

7. A measurement apparatus as claimed in claim 1, wherein the sensing apparatus comprises an airflow pathway from an outside of the apparatus into the first measurement chamber, and out of the first measurement chamber into the second measurement chamber, and out of the second measurement chamber to the outside, the sensing apparatus further comprising an airflow generator for moving air along the airflow pathway.

8. A measurement apparatus as claimed in claim 1, wherein the sensing apparatus further includes an air dryer to remove moisture from air passing through the compensation chambers, and wherein the sensing apparatus comprises an airflow pathway from an outside of the apparatus into the first measurement chamber, and out of the first measurement chamber into the second measurement chamber, and out of the second measurement chamber into the air dryer, and out of the air dryer into the first compensation chamber, and out of the first compensation chamber into the second compensation chamber, and out of the second compensation chamber to the outside, the sensing apparatus further comprising an airflow generator for moving air along the airflow pathway.

9. A measurement apparatus as claimed in claim 8, wherein the sensing apparatus further includes a relative humidity sensor on the airflow pathway between the air dryer and an inlet to the first compensation cylinder, the relative humidity sensor being configured to display a relative humidity between zero and one hundred percent of the air entering the first compensation cylinder from the air dryer, whereby the functioning of the air dryer can be easily monitored.

10. A tritium-in-air measuring apparatus for measuring a concentration of tritium in air, the measuring apparatus comprising:
  a sensing apparatus for sensing the concentration of tritium in the air and producing at least one signal representing the concentration; and
  a signal processing apparatus, operatively connected to the sensing apparatus, for receiving the signal, processing the signal, and outputting an indication of the concentration of tritium,
  the sensing apparatus comprising four equal-dimensioned ion chambers, each ion chamber comprising a cylinder, and the four ion chambers comprising a first measurement chamber, a second measurement chamber, a first compensation chamber and a second compensation chamber;
  wherein the sensing apparatus further includes an air dryer to remove moisture from air passing through the compensation chambers, and wherein the sensing apparatus comprises an airflow pathway from an outside of the apparatus into the first measurement chamber, and out of the first measurement chamber into the second measurement chamber, and out of the second measurement chamber into the air dryer, and out of the air dryer into the first compensation chamber, and out of the first compensation chamber into the second compensation chamber, and out of the second compensation chamber to the outside, the sensing apparatus further comprising an airflow generator for moving air along the airflow path; and
  the sensing apparatus further comprising a pressure compensation apparatus for determining a measurement normalization coefficient for normalizing a measured signal, and a compensation normalization coefficient for normalizing a compensation signal.

11. The measurement apparatus as claimed in claim 10, wherein the pressure compensation apparatus comprises
  a first absolute pressure sensor for measuring the absolute pressure at an inlet to the first measurement chamber, a second absolute pressure sensor for measuring an absolute pressure at an inlet to the first compensation chamber, and a differential pressure sensor for measure pressure difference between an outlet of the second measurement chamber and the inlet of the first measurement chamber.

12. The measurement apparatus as claimed in claim 11, wherein the measurement normalization coefficient is determined according to the formula:

$$P_{ATM}/(AP_1+DP/2)$$

wherein $P_{ATM}$ is mean atmospheric pressure at sea level, $AP_1$ is the pressure measured by the first absolute pressure sensor, and DP is the pressure difference measured by the differential pressure sensor.

13. The measurement apparatus as claimed in claim 11, wherein the compensation normalization coefficient is determined according to the formula:

$$P_{ATM}/(AP_2+DP/2)$$

wherein $P_{ATM}$ is mean atmospheric pressure at sea level, $AP_2$ is the pressure measured by the second absolute pressure sensor, and DP is the pressure difference measured by the differential pressure sensor.

14. The measurement apparatus as claimed in claim 11, wherein the measurement normalization coefficient is determined according to the formula:

$$P_{ATM}/(AP_1+DP/2)$$

wherein $P_{ATM}$ is mean atmospheric pressure at sea level, $AP_1$ is the pressure measured by the first absolute pressure sensor, and DP is the pressure difference measured by the differential pressure sensor;

and wherein the compensation normalization coefficient is determined according to the formula:

$$P_{ATM}/(AP_2+DP/2)$$

wherein $P_{ATM}$ is mean atmospheric pressure at sea level, $AP_2$ is the pressure measured by the second absolute pressure sensor, and DP is the pressure difference measured by the differential pressure sensor.

* * * * *